Figure 9:
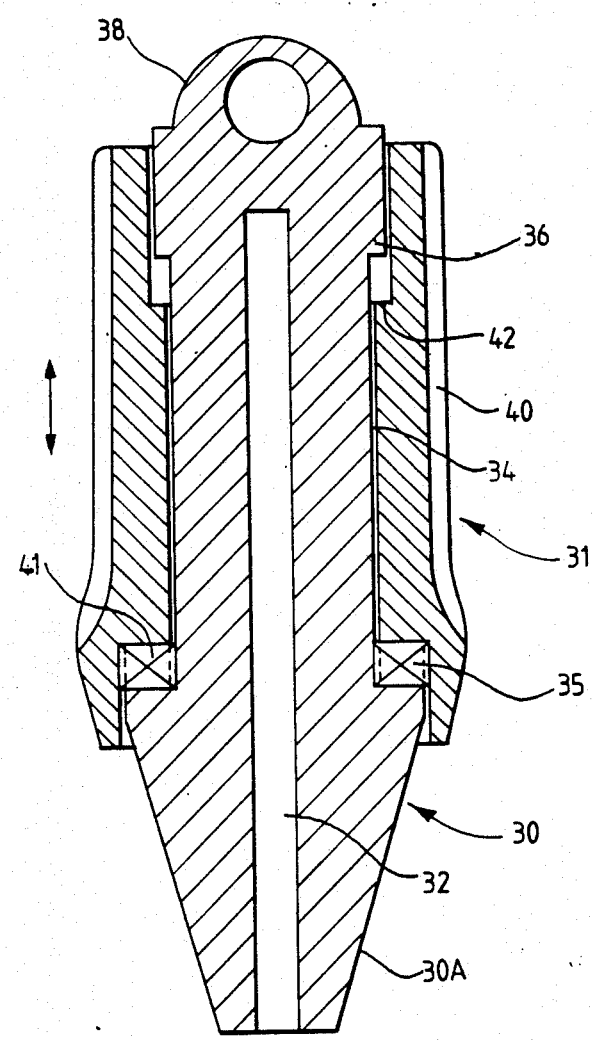

United States Patent [19]

Filhol

[11] Patent Number: 4,692,116

[45] Date of Patent: Sep. 8, 1987

[54] DENTAL PIN AND HOLDER

[76] Inventor: Stuart J. Filhol, Castlefreke, County Cork, Ireland

[21] Appl. No.: 787,981

[22] Filed: Oct. 16, 1985

[30] Foreign Application Priority Data

Oct. 16, 1984 [GB] United Kingdom ................. 8426117
Jan. 5, 1985 [GB] United Kingdom ................. 8500283

[51] Int. Cl.$^4$ ............................................. A61C 5/04
[52] U.S. Cl. .................................................... 433/225
[58] Field of Search ............................. 433/225, 165

[56] References Cited

U.S. PATENT DOCUMENTS

| | | | |
|---|---|---|---|
| 3,576,076 | 4/1971 | Weissman | 433/165 |
| 3,751,176 | 8/1973 | Hollen | 433/165 |
| 4,053,982 | 10/1977 | Weissman | 433/225 |
| 4,451,237 | 5/1984 | Filhol | 433/225 |
| 4,465,463 | 8/1984 | Hisonolde | 433/225 |
| 4,500,296 | 2/1985 | Friedman | 433/225 |

Primary Examiner—Robert Peshock
Attorney, Agent, or Firm—Gifford, Groh, VanOphem, Sheridan, Sprinkle and Dolgorukov

[57] ABSTRACT

A dental pin having a threaded portion for insertion into a tooth is formed with a shank which has portions inclined relative to the threaded portion and to each other. The threaded portion and shank are of integral construction and the shank is of zig-zag shape.

A holder for the pin can take several forms each with a bore for receiving the shank releasably but in driving engagement with the holder.

The holder may take a form suitable for use with a dental handpiece or for manual insertion of the pin.

The invention also provides a holder with a ratchet mechanism for manual insertion of the pin.

14 Claims, 9 Drawing Figures

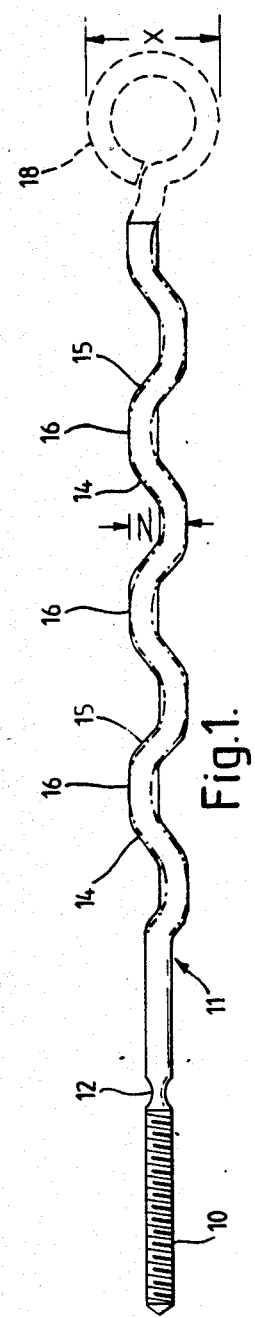
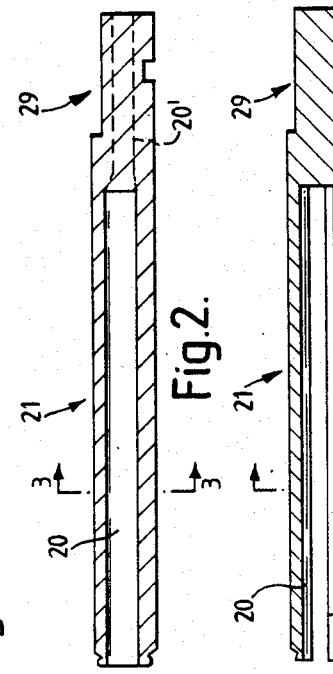
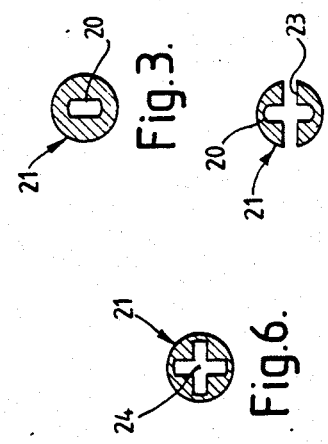

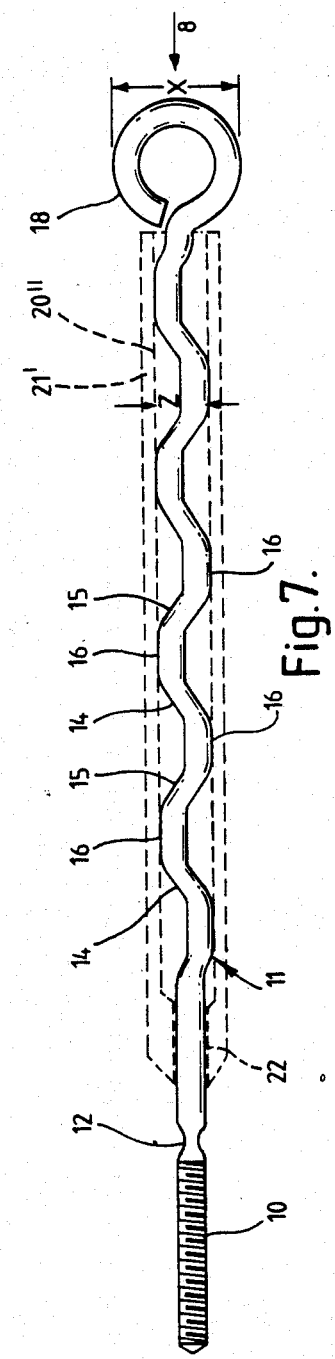
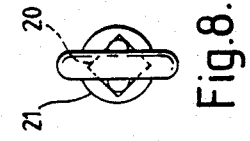
Fig. 7.
Fig. 8.

DENTAL PIN AND HOLDER

This invention relates to dental pins and in particular to dental pins having a threaded portion for insertion into a tooth, and to means for holding the pins during insertion.

Various dental pins with threaded portions have been proposed some of which are intended to be inserted with a dental handpiece. Of these dental pins many have utilised an arrangement in which the threaded portion to be inserted into a tooth is releasably connected to a shank portion usually through a reduced section neck whereby the neck shears when the resistance to rotation of the threaded pin portion reaches a predetermined level.

In inserting such pins some are directly engaged through the shank into a standard dental handpiece with the conventional latching means. In some cases the pin consists of a length of wire having means at one end for connecting the pin to a holder or adapter, the other end being threaded for insertion into the dentine of a tooth, such as in European Pat. No. 0056198. Other relevant arrangements are disclosed in European Pat. No. 0039202, British Pat. No. 2016631 and U.S. Pat. No. 4,155,162.

It is an object of the invention to provide an improved dental pin of the kind described and holding means for holding the pin during insertion.

According to a first aspect of the invention a dental pin comprises an elongate threaded pin portion for insertion into a tooth and a shank releasably connected to the threaded portion, the shank including at least two shank portions whose axes are inclined at an acute angle to the axis of the threaded portion and the two shank portions are inclined in opposite directions to one another.

The shank portions may be of zig-zag shape and formed of rod integral with the threaded pin portion.

Preferably the inclined portions have interposed between them a portion whose axis is parallel to that of the threaded portion. Conveniently a succession of inclined portions extend along at least part of the shank.

The end of the shank remote from the pin portion may be formed with an enlarged portion such as a loop.

Preferably the inclined portions lie in the same plane.

The invention also provides a dental pin and adapter combination in which the dental pin takes the form defined according to the first aspect of the invention and the adapter comprises an elongate element having a longitudinal bore whose cross-section is profiled to receive the shank and to prevent relative rotation between the adapter and the shank during driving of the pin into a hole in a tooth by engagement of the inclined portions with the walls of the bore.

For example the bore may be of square, rectangular, oval or elliptical cross-section whereby the inclined portions engage in opposite corners of the bore.

The adapter may be arranged to be fitted into a dental handpiece for driving the pin portion into a tooth in which case the adapter may be formed with an outer profile to be latched into the handpiece in conventional manner.

The combination may include an adapter which is in two relatively rotatable portions, an inner portion having said bore and an outer portion, the two portions having coupling means therebetween whereby the outer portion is selectively coupled for rotation with the inner portion to rotate the dental pin during insertion thereof.

According to another aspect the invention provides a dental pin and adapter combination comprising a dental pin having a threaded pin portion for insertion into a tooth and a shank portion, and an adapter for receiving the shank portion for connection with the dental pin characterised in that the adapter is in two relatively rotatable portions, an inner portion to which the dental pin is connected and an outer portion, the two portions having coupling means therebetween whereby the outer portion is selectively coupled for rotation with the inner portion to rotate the dental pin during manual rotation of the adapter.

Further features of the invention will appear from the following description of embodiments of the invention given by way of example and with reference to the drawings, in which:

FIG. 1 is a side elevation of a dental pin,

FIG. 2 is a longitudinal cross-section to a reduced scale to that of FIG. 1 through an adapter for locating the pin of FIG. 1 in a dental handpiece, FIG. 3 is a cross-section on the line 3—3 of FIG. 2, FIG. 4 is a longitudinal cross-section of an alternative form of adapter for the pin of FIG. 1, FIG. 5 is a cross-section on the line 5—5 in FIG. 4, FIG. 6 is a cross-section of an adapter similar to that of FIG. 2 but having a bore of different cross-sectional shape, FIG. 7 is a side elevation of a dental pin similar to that of FIG. 1 associated with another form of adapter, FIG. 8 is a view in the direction 8 in FIG. 7, and FIG. 9 is a longitudinal cross-section of a hand operated adapter for the pin of FIG. 1.

Referring to the drawings and firstly to FIG. 1 a dental pin includes an elongate threaded pin portion 10 and a shank portion 11. The portions 10 and 11 are integral with one another and formed of a single piece of circular-section wire or rod having a diameter corresponding to the desired diameter of the pin portion 10. However the wire or rod can have other cross-sections such as hexagonal.

The pin portion 10 is formed with a screw-thread along its length to enable the portion to be driven into a preformed hole in the tooth to form a self-tapping engagement with the hole during insertion.

The pin portion 10 is connected to the shank portion 11 through a reduced-section or neck portion 12 arranged so that when the pin portion 10 reaches the base of the pre-formed hole in a tooth the resistance to rotation of the pin causes the pin portion 10 to be sheared off from the shank portion at the reduced-section portion 12.

At its end adjacent the neck portion 12 the shank portion 11 has its axis aligned with the pin portion 10. There are then formed in the shank portion a succession of oppositely-inclined and intermediate portions 14, 15 and 16 forming a zig-zag shape. The oppositely-inclined portions 14 and 15 lie in the same plane and have their axes inclined at an acute angle to the axis of the pin portion 10 and the intermediate portions 16 have their axes parallel to and displaced to one side of the the axis of the pin portion 10. Intermediate portions 16 are located between successive inclined portions 14 and 15 so that the axes of the successive intermediate portions 16 are located to one side and to the other of the axis of the pin portion in progressing along the shank portion 11.

If desired the intermediate portions 16 may be omitted so that there are oppositely-inclined portions 14 and 15 only presenting a succession of oppositely directed V-shaped elements, as shown in chain lines in FIG. 1, or a single V-shaped portion. The angles of inclination of the inclined portions 14 and 15 may be different to those shown and in some cases the angles of inclination may be up to 90° from the central axis of the pin portion 10.

The arrangement of the inclined portions 14 and 15 and of the intermediate portions 16 (if present) is such that they will be accommodated in a generally rectangular bore 20 formed in an adapter 21 (FIGS. 2 and 3). In this position the intermediate portions 16 are lodged at opposite sides of the rectangular bore thereby engaging the walls of the bore and preventing relative rotation between the dental pin and the adapter 21.

Although in FIG. 3 the bore 20 is shown as being rectangular and, in this case, having rounded ends, the bore may be of other cross-section such as square, elliptical or oval.

The adapter 21, as shown, is for fitting into a standard dental handpiece having a conventional latching mechanism and has a generally cylindrical body. The upper end of the adapter is provided with the conventional flat and groove 29 for latching the adapter into the handpiece.

The pin portions 14, 15 and 16 are a close fit in the bore 20 so that due to the fit and the resilience of the portions 14, 15 and 16 the pin is retained in the bore 20 during use.

The adapter illustrated in FIGS. 2 and 3 is conveniently formed as a plastics moulding or as a die casting as shown. Alternatively the adapter is made from metal tubing, for example brass, initially cylindrical having a cylindrical opening. The opening can be formed into a generally rectangular or elliptical cross-section, at least over the end remote from the flat and groove 29, by partially flattening the tube. Prior to flattening the tube said end may be reduced in diameter over its outer periphery so that when flattened the maximum external dimension is no greater than the initial outer diamter of the tube. Alternatively, or in addition, the flattened portion may be machined externally to reduce the maximum outer dimension to that desired.

In the case in which a tube is used to make the adapter the adapter in its finished form will have an openended bore of which a portion is flattened and of generally rectangular section and a portion at the end on which the flat and groove 29 are formed is of circular section, as shown by dotted lines 20' in FIG. 2.

The pin shank 11 shown in FIG. 1 may be formed with a loop 18 at its end remote from the pin portion 10, as shown in chain lines in FIG. 1 but in a plane at a right angle to the portions 14, 15, 16. In this form the pin can be located in the adapter of FIGS. 4 and 5 in which an opening 20 corresponding to the bore of the FIG. 2 embodiment is formed and a slot 23 extends across the opening from one side to the other. Thus the body of the adapter is split longitudinally into two halves along a length sufficient to receive the pin of FIG. 1 having the loop 18.

When the pin is located in the adapter the loop 18 is received in the slot 23 and the portions 14, 15 and 16 in the opening 20. As shown the loop 18 has a outer dimension x greater than the distance z between opposite sides of the portions 16.

When the adapter of FIG. 2 has a bore 24 of the cross-section shown in FIG. 6 in which the bore is of X-shape it is able to receive a pin with a loop such as shown at 18 in FIG. 1 but in a plane at a right angle to that of the portions 14, 15, 16 and of about the same width as the dimension z (FIG. 1) of the portions 14, 15, 16. Alternatively successive portions 14, 15, 16 of the shank do not lie all in the same plane but are displaced through 90° relative to one another to lie in two planes. In this arrangement the pin may be located in a bore 24 such as shown in FIG. 6 with or without any loop 18.

The adapters of FIGS. 2 and 4 can be modified to be operable manually rather than by dental handpiece. The outer profile of the adapters would be enlarged to be more adapted for gripping with the fingers, or the adapters are locatable in the bore of a hand wrench device (not shown) the bore having at its base a flat for location with the flat at the end of the adapter. In this way the adapter rotates with the hand wrench device during insertion of a pin.

Referring now to FIGS. 7 and 8 a dental pin is shown which is substantially the same as the pin of FIG. 1 and having the loop 18 at one end. The pin is shown associated with a holder or adapter 21' having a rectangular bore 20'' which in this case is open-ended so that the pin portion 10 may be inserted along and through the bore until the loop 18 is close to or partially located in the end of the bore 20''. In this position the portions 16 of the shank are lodged in opposite corners of the bore 20'' as seen in FIG. 8 thereby engaging the walls of the bore and preventing relative rotation between the dental pin and the adapter 21'. The adapter 21' is generally cylindrical and extends from a position adjacent the loop 18 at one end to adjacent the neck portion 12 at the other end. At said other end the adapter may taper inwardly and have a circular bore 22 for locating the stem. At the end adjacent the loop 18 the adapter may have a slot for locating the loop. Although as shown in FIG. 7 the loop 18 is in the same plane as the portions 14, 15 and 16, the loop 18 is preferably displaced through 90° about the pin axis relative to the plane of the portions 14, 15 and 16.

The adapter 21' can be formed so as to be suitable for manual insertion of the pin portion 10. In this case a portion of the adapter is formed with an enlarged circular section to be grasped between the fingers for rotating the adapter and associated pin during insertion.

The pin may be retained in the adapter against movement upwards along the bore during use by making the end of the shank portion adjacent the loop 18 a close fit in the bore, by engaging a portion of the adapter through the loop 18, or by having a member on the adapter or on the handpiece which is located over the loop 18, or be engagement of the bent portions 14, 15 and 16 with a portion of the bore 20''.

The adapter 21' may form a driven member which is housed in a modified dental handpiece, drive being transmitted directly to the adapter by, for example, forming gear teeth, on the adapter, to rotate the adapter about the axis of its bore 20'' by engagement of handpiece drive means with the adapter gear teeth. Referring now to FIG. 9 a manually-operated holder for dental pins is shown. The holder includes an inner member 30 and an outer member 31 in the form of a sleeve. The inner member 30 has a longitudinal bore 32 of rectangular-section along its length, for example of the cross-section shown in FIG. 3 or FIG. 6. Over its outer surface the member 30 is of generally circular-section tapering towards the lower end 30A and having a cylindrical portion 34 with ratchet teeth 35 at one end of the portion 34 and a shoulder 36 at the other end.

At the upper end of the member 30 is formed a loop 38 for receiving a retaining thread (not shown).

The outer member 31 is generally tubular and is located around and is retained on the portion 34 of the inner member. The outer surface of the member 31 is formed with longitudinal grooves 40 whereby the member 31 is readily gripped by the operator's fingers and turned during operation of the holder. However the outer surface can be formed with other means to provide a gripping surface. On its internal surface the outer member 31 is formed with ratchet teeth 41 for engagement with the ratchet teeth 35 of the inner member 30. The outer member 31 has a shoulder 42 and is movable relative to the inner member 30 in the axial direction of the holder so that when moved toward the lower end 30A of the inner member 30 the ratchet teeth 35 and 41 are engageable (as shown in FIG. 9). When moved axially in the opposite direction the outer member 31 moves to a position in which the member 31 is freely rotatable relative to the inner member 30 about the holder axis and the shoulders 36 and 42 move towards each other. The shoulders may be replaced by ratchet teeth interengageable during reverse rotation of the members.

The ratchet teeth 35 and 41 are so formed that rotation of the outer member 31 causes rotation of both inner and outer members together in one direction only when the teeth 35 and 41 are engaged. The inner and outer members may rotate together in the opposite direction only if ratchet teeth are provided on the shoulders 36 and 42. Thus the pair of ratchet teeth 35 and 41 is unidirectional and rotation of the outer member in the opposite direction causes the teeth to ride over one another. For this purpose the teeth of the ratchets have alternating inclined and upright faces the upright teeth faces engaging in one direction of rotation and the inclined faces being operative in the opposite direction to prevent rotation of the inner and outer members in said direction by the inclined faces sliding over one another. This enables the operator to retain hold of the holder during a return movement of the member 31 during which the member 30 is not rotatable.

This arrangement of the ratchet teeth is to enable the holder to be operated to enable the pin in the holder to be rotated with the inner and outer members of the holder when the outer member is pressed down towards the lower end of the holder. This action inserts the pin in a tooth and the outer member is rotated in one direction. When the outer member is rotated in the return movement in the opposite direction with the outer member in the lower position no rotation of the pin occurs due to the unidirectional driving action of the teeth 35 and 41. However if the outer member 31 is moved to its upper position relative to the inner member 30 and the shoulders 36 and 42 include teeth and the member is rotated in said opposite direction the pin is again rotated with the holder but this time in a direction to unscrew the pin from the tooth, if desired.

The holder shown in FIG. 9 is adapted for use with the pin shown in FIG. 1 without the loop 18. The pin is located in the holder by insertion of the pin along the bore 32.

Although the holder shown in FIG. 9 is arranged for use with the pin of FIG. 1 it will be understood that the holder can be adapted for use with other pins which can be releasably secured or united with the inner member.

For example the inner member can be provided with a slot or bore at its lowre end in which a pin including a threaded portion and a shank can be secured.

The holder is preferably formed as a two-part plastics moulding but other methods of construction can be employed.

In each of the dental pin and adapter/holder combinations described the shank portion 11 is located in the associated bore with sufficient firmness that the pin is easily located in the bore but not too slack that the pin can become inadvertently dislodged from the bore. This is due to the close fit of the shank portion 11 with the bore and the resilience of the zig-zag portions 14, 15, 16 and of the holder/adapter. In the embodiments described the holder/adapter is conveniently of plastics but it may be of metal particularly that of FIGS. 4 and 5.

In the embodiments of FIGS. 1–6 and FIG. 9 the pin portion 10 can be arranged to extend a selected amount from the end of the associated bore according to the user's preference and there will normally still be anough resistance against movement along the bore to screw the pin into a hole in a tooth.

What I claim as my invention and desire to secure by Letters Patent of the United States is:

1. A dental pin comprises an elongate threaded pin portion for insertion into a tooth and a shank releasably connected to the threaded portion, wherein the shank includes at least two shank portions whose axes are inclined at an acute angle to the axis of the threaded portion and the two shank portions are inclined in opposite directions to one another.

2. A dental pin according to claim 1 wherein the shank portions are of zig-zag shape.

3. A dental pin according to claim 1 wherein the shank is formed of rod integral with the threaded pin portion.

4. A dental pin according to claim 1 wherein the inclined portions have interposed between them a portion whose axis is parallel to that of the threaded portion.

5. A dental pin according to claim 1 wherein the inclined portions lie in the same plane.

6. A dental pin according to claim 1 wherein the end of the shank remote from the pin portion is formed with an enlarged portion such as a loop.

7. A dental pin and adapter combination comprises a dental pin as claimed in claim 1 and an adapter, the adapter including an elongate element having a longitudinal bore whose cross-section is profiled to receive the dental pin shank and to prevent relative rotation between the adapter and the shank during driving of the pin into a hole in a tooth.

8. A combination according to claim 7 wherein the bore is of square, rectangular, oval or elliptical cross-section whereby the inclined portions extend across the longest dimension of the bore.

9. A combination according to claim 7 wherein the adapter is formed with means for latching the combination into a dental handpiece.

10. A combination according to claim 7 wherein the adapter is provided with means for manually grasping and rotating the combination.

11. A combination according to claim 10 wherein the adapter is in two relatively rotatable portions, an inner portion having said bore and an outer portion, the two portions having coupling means therebetween whereby the outer portion is selectively coupled for rotation with the innner portion to rotate the dental pin during insertion thereof.

12. A combination according to claim 7 wherein the adapter is formed with opposed longitudinal slots communicating with the bore.

13. A combination according to claim 7 wherein the bore is open-ended and the dental pin shank is formed with a loop at the end remote from the pin portion which, when assembled in the bore, engages with one end of the bore.

14. A combination according to claim 7 wherein the bore in the adapter is of X shape in cross-section for receiving the shank and any enlargement at the end of the shank remote from the pin portion.

* * * * *

UNITED STATES PATENT AND TRADEMARK OFFICE
CERTIFICATE OF CORRECTION

PATENT NO. : 4,692,116
DATED : September 8, 1987
INVENTOR(S) : Stuart J. Filhol

It is certified that error appears in the above-identified patent and that said Letters Patent is hereby corrected as shown below:

Column 2, line 63, delete "the" first occurrence.

Column 4, line 53, "be" should read --by--.

Column 6, line 2, "lowre" should read --lower--.

Signed and Sealed this

Twenty-ninth Day of March, 1988

Attest:

DONALD J. QUIGG

Attesting Officer      Commissioner of Patents and Trademarks